US012232739B2

United States Patent
Gonzalez Chapa et al.

(10) Patent No.: US 12,232,739 B2
(45) Date of Patent: Feb. 25, 2025

(54) SURGICAL CUTTING TOOLS AND CUTTING TOOL ATTACHMENT MECHANISMS, AND RELATED SYSTEMS AND METHODS

(71) Applicant: Monogram Orthopaedics Inc., Austin, TX (US)

(72) Inventors: Gerardo Angel Gonzalez Chapa, Austin, TX (US); Scott Hudson, Pflugerville, TX (US)

(73) Assignee: Monogram Orthopaedics Inc., Austin, TX (US)

( * ) Notice: Subject to any disclaimer, the term of this patent is extended or adjusted under 35 U.S.C. 154(b) by 0 days.

(21) Appl. No.: 18/758,815

(22) Filed: Jun. 28, 2024

(65) Prior Publication Data
US 2024/0350146 A1    Oct. 24, 2024

Related U.S. Application Data

(63) Continuation of application No. PCT/US2023/060144, filed on Jan. 5, 2023.
(Continued)

(51) Int. Cl.
*A61B 17/122*    (2006.01)
*A61B 17/32*    (2006.01)

(52) U.S. Cl.
CPC ........ *A61B 17/122* (2013.01); *A61B 2017/320082* (2017.08); *A61B 2217/002* (2013.01)

(58) Field of Classification Search
CPC .............. A61B 34/30; A61B 2217/002; A61B 2017/320082; A61B 17/122
See application file for complete search history.

(56) References Cited

U.S. PATENT DOCUMENTS

| | | | |
|---|---|---|---|
| 6,113,618 A * | 9/2000 | Nic ............ | B23D 61/123 |
| | | | D24/146 |
| 8,100,912 B2 * | 1/2012 | Marietta ........ | A61B 17/142 |
| | | | 606/176 |

(Continued)

OTHER PUBLICATIONS

International Search Report and Written Opinion of International Search Authority, issued by the U.S. Patent & Trademark Office for PCT Appl. PCT/US2023/060144, 8 Pages, dated Jun. 5, 2023.

*Primary Examiner* — Kevin T Truong
*Assistant Examiner* — Diana Jones
(74) *Attorney, Agent, or Firm* — Heslin Rothenberg Farley & Mesiti P.C.

(57) ABSTRACT

A cutting tool and an attachment mechanism configured to removably securely couple the cutting tool and a cutting instrument together. The cutting tool comprises a tang end portion, a tip end portion, and a cutting edge on the tip end portion. The attachment mechanism comprises a first and second clamping members with first and second engagement surfaces, respectively. The second clamping member further comprises a pair of axially-spaced projections extending and a pair of laterally-spaced projections extending past the second engagement surface. The attachment mechanism further comprises an adjustment mechanism configured to selectively adjust the distance between the first and second engagement surfaces. The tang end portion comprises an axially extending coupling slot and a pair of elastically-deformable securement members at lateral sides that extend laterally outward as they extend axially from the tang end portion toward the tip end portion.

20 Claims, 12 Drawing Sheets

Related U.S. Application Data

(60) Provisional application No. 63/296,849, filed on Jan. 5, 2022.

(56) References Cited

U.S. PATENT DOCUMENTS

| | | |
|---|---|---|
| 10,456,142 B2 | 10/2019 | Shiels |
| 2006/0206100 A1* | 9/2006 | Eskridge .............. A61B 17/142 606/1 |
| 2008/0027449 A1 | 1/2008 | Gundlapalli |
| 2009/0138017 A1* | 5/2009 | Carusillo ............... A61B 17/14 606/82 |
| 2012/0041443 A1 | 2/2012 | Landon |
| 2015/0128402 A1* | 5/2015 | Wang ................... A61B 17/142 29/453 |
| 2021/0353303 A1 | 11/2021 | Gayle |

* cited by examiner

SURGICAL CUTTING TOOLS AND CUTTING TOOL ATTACHMENT MECHANISMS, AND RELATED SYSTEMS AND METHODS

CROSS-REFERENCE TO RELATED APPLICATION

The present application is a bypass continuation of International Application No. PCT/US2023/060144, published as WO 2023/133447, entitled Surgical Cutting Tools and Cutting Tool Attachment Mechanisms, and Related Systems and Methods, filed on Jan. 5, 2023, which perfects and claims priority benefit of U.S. Provisional Application No. 63/296,849, entitled Surgical Cutting Tools and Cutting Tool Attachment Mechanisms, and Related Systems and Methods, filed on Jan. 5, 2022, the entireties of which are hereby expressly incorporated herein by reference.

FIELD OF THE DISCLOSURE

The following disclosure relates generally to cutting instrumentalities. More particularly, the following disclosure relates to instruments for cutting bone or other tissue that include a surgical cutting tool and an attachment mechanism adapted to be operatively coupled together such that the cutting tool and the attachment mechanism are reliably properly and securely removably coupled together

BACKGROUND

Typically, a cutting tool is coupled with a cutting instrument that facilitates movement of the cutting tool in some fashion to cut tissue. Many cutting instruments are configured to couple with a cutting tool, and facilitate movement of the cutting tool so that one or more cutting edge of the cutting tool effectuates cutting with the material engaged therewith.

Some cutting instruments are manual cutting instruments that are manually manipulated by a user. Other cutting instruments are powered cutting instruments that include a power source (e.g., an electric motor) that provides at least some movement of the cutting tool along a cutting pathway defined by the cutting edge. Some such powered cutting instruments require at least some manual manipulation of the cutting tool to execute cutting of tissue (or another material). For example, some powered cutting instruments are configured as handheld or hand-guided instruments that move the cutting tool along its cutting pathway, but require the user to manually guide the moving cutting tool to and/or through the tissue to cut the tissue (or another material). Other powered cutting instruments are coupled to, or form part of, a surgical robot that translates a moving cutting tool to and/or through the tissue (or another material) without a user manually engaging the cutting instrument.

Cutting tools are typically made from materials that are harder than those they are to be used on. Many different cutting tool configurations exist, such as but not limited to cutting blades and cutting bits. A typical saw blade has a thin, flat, elongated shape with a cutting edge at one end. The thin, flat design minimizes the size of the required pathway and allows the blade to cut an accurate, straight cut. The cutting edge is generally oriented along a direction that is orthogonal to the direction of blade elongation and contains a plurality of teeth and/or abrasives. Thus, when the blade is inserted into the pathway, the cutting edge can be pressed against the surface of the bone that requires resection.

Cutting blades are configured to cut when moved, such as in a reciprocating motion (along forward and/or back strokes), along a linear direction (colinear with the cutting edge), along a plane (e.g., two dimensions) or in a three-dimensional pattern. For example, some blades are constructed to pivot back and forth, or oscillate, in the plane in which the blade is oriented, as illustrated by the exemplary cutting blade 1 shown in FIG. 1. The cutting blade 1 may be designed to oscillate linearly laterally or in an arc extended along the plane of the blade 1. This type of blade 1 is referred to as a sagittal saw blade. The exemplary sagittal saw blade 1 is provided with teeth that extend forward from the distal end of the blade body. Other blades are configured to cut while moving back and forth along their longitudinal axes. Such type of blades are known as a reciprocating saw blade, and is provided with teeth that extend outwardly from a side edge of the blade body.

An end portion of saw blades commonly includes a tang or hub portion 2 configured to attach with a cutting instrument, such as a powered cutting instrument, as shown in with the cutting blade 1 of FIG. 1. Typically, a cutting instrument has a chuck or other attachment mechanism configured to mate with the tang portion 2 and removably secure the saw blade 1 (or other cutting tool) and the cutting instrument together. For such a cutting instrument to function properly, the tang portion 2 of the cutting blade 1 needs to be properly engaged with the attachment mechanism. Most attachment mechanisms of cutting instruments sequentially engage the tang portion 2 of the saw blade 1 by the tang portion 2 first being inserted into the attachment mechanism, and then the attachment mechanism manipulated (typically manually) to lock the saw blade 1 to the cutting instrument via the attachment mechanism.

Cutting tool attachment mechanisms of typical cutting instruments require the user to use two hands to properly couple the cutting tool and cutting instrument. For example, it is often necessary to surgically cut or resect a bone, cartilage and/or other tissue of a patient (e.g., a mammalian patient), such as during a surgical procedure. A surgeon or technician often does not have both of their hands readily available during surgical procedures, and thereby such attachment mechanisms are problematic.

Also, many attachment mechanisms allow the cutting tool to move out of position until it is manually fully secured, resulting in improper cutting tool positions or an unsecure coupling with the cutting instrument which can impair cutting accuracy, prevent the cutting instrument and/or tool from functioning properly and be dangerous.

Further, many cutting tool attachment mechanisms of cutting instruments rely on imprecise methods of placement, such as one or more visual indication on the cutting tool. For example, as shown in FIG. 1, many saw blades 1 include a visual indication 3 on or adjacent to the tang portion 2 that indicates the extent of the tang portion 2 that must be engaged within a corresponding attachment mechanism to properly secure the saw blade 1 with the cutting tool. Such attachment mechanisms rely on the visual indication on the cutting tool to alert the user that they have fully and/or properly inserted the cutting tool into the attachment mechanism. In robotic applications, additional steps, such as registration of the position of the cutting tool, may be required to ensure proper placement of the cutting tool. These visual aids are not always effective means of determining proper placement of the cutting tool.

While certain aspects of conventional technologies have been discussed to facilitate disclosure of Applicant's inventions, the Applicant in no way disclaims these technical aspects, and it is contemplated that the inventions may encompass one or more conventional technical aspects.

In this disclosure, where a document, act or item of knowledge is referred to or discussed, this reference or discussion is not an admission that the document, act or item of knowledge or any combination thereof was, at the priority date, publicly available, known to the public, part of common general knowledge, or otherwise constitutes prior art under the applicable statutory provisions; or is known to be relevant to an attempt to solve any problem with which this specification is concerned.

SUMMARY

The present inventions may address one or more of the problems and deficiencies of current cutting tools and cutting instruments and attachment mechanisms thereof. However, it is contemplated that the inventions may prove useful in addressing other problems and deficiencies in a number of technical areas. Therefore, the claimed invention(s) should not necessarily be construed as limited to addressing any of the particular problems or deficiencies discussed herein.

The present disclosure is generally directed to current cutting tools, cutting instruments, cutting tool attachment mechanisms, and related systems and methods. The present disclosure provides cutting instrument attachment mechanisms and cutting tools that cooperatively allow a user to both couple and decouple a cutting tool with a cutting instrument via only one hand of a user. Furthermore, the present disclosure provides cutting instrument attachment mechanisms and cutting tools that cooperatively ensure that a cutting tool is securely and properly engaged with an attachment mechanism by mitigating the risk of cutting tool back-out and/or misalignment prior to fully securing the cutting tool via the attachment mechanism.

In some embodiments, the present disclosure provides for a cutting tool attachment mechanism that allows a user to securely and reliably couple a cutting tool (such as a cutting blade) and a cutting instrument (such as a powered cutting instrument) together. The cutting tool attachment mechanisms provides for ease of placement, accuracy of placement, mitigated risk of poor placement, and ease of removal of a cutting tool with a cutting instrument.

The cutting tool attachment mechanisms and corresponding cutting tools include features that ensure full and proper engagement of the cutting instrument via mechanical interfaces which provide tactile and auditory feedback to a user. The features of the cutting tool attachment mechanisms and corresponding cutting tools also relatively securely engage a cutting tool prior to fully locking the cutting tool to the cutting instrument.

In some embodiments, a cutting tool, such as a cutting blade (e.g., a sagittal bone saw blade) includes securement members or "fingers." Upon securely coupling the cutting tool and a corresponding cutting tool attachment mechanism (which may be coupled to a cutting instrument), the securement members are elastically deformed or depressed into a deformed state during initial insertion of the cutting tool into the cutting tool attachment mechanism, and resiliently deform from the deformed state into a locking state upon the cutting tool being fully inserted into the cutting tool attachment mechanism. In the locking state of the securement members, the cutting tool is reliably and securely releasably coupled with the cutting tool attachment mechanism (and thereby the cutting instrument) as the securement members provide a locking force that prevents backout of the cutting tool from the attachment mechanism (even prior to adjustment of the attachment mechanism that locks the cutting tool within the attachment mechanism). The securement members generates tactile and auditor feedback to the user that the cutting tool is properly seated in the attachment mechanism such that the cutting tool is reliably and securely releasably coupled with the attachment mechanism (and thereby the cutting instrument). Further, the securement members, in their locking state, prevent backout of the cutting tool prior to adjustment of the attachment mechanism such that it locks the cutting tool within the attachment mechanism.

It is noted that the cutting tool may be any cutting tool, such as but not limited to a surgical cutting tool configured to cut or resect tissue. In one exemplary embodiment, the cutting tool is a cutting blade or saw (e.g., a sagittal surgical saw blade). Similarly, the cutting instrument may be any cutting instrument configured to couple to the cutting tool and facilitate use of and/or utilize the cutting tool to cut a material, such as but not limited to a powered cutting tool. In one exemplary embodiment, the cutting instrument is a powered cutting instrument that reciprocates or rotates the cutting tool in a direction extending along the cutting edge thereof (e.g., along a direction that the cutting edge is configured to cut), such as a powered sagittal saw. In some such embodiments, the powered cutting instrument is a handheld power tool. In some embodiments, the powered cutting instrument is part of or coupled to a robot, such as a surgical robot.

In one aspect, the present disclosure provides a system comprising a cutting tool and a cutting instrument. The cutting tool comprises a tang end portion, a tip end portion, and a cutting edge on the tip end portion configured to cut material upon movement of the cutting tool with the cutting edge in engagement with the material, the cutting tool having an axial length extending between the tang end portion and the cutting edge. The cutting instrument comprises an attachment mechanism configured to removably securely couple the cutting tool and the cutting instrument together, the cutting instrument configured to effectuate or facilitate the movement of the cutting tool. The attachment mechanism comprises: a first clamping member comprising a first engagement surface; a second clamping member comprising a second engagement surface, a pair of axially-spaced projections extending past the second engagement surface and a pair of laterally-spaced projections extending past the second engagement surface; and an adjustment mechanism configured to selectively adjust the distance between the first and second engagement surfaces via relative movement between the first and second clamping member. The tang end portion of the cutting tool comprises an axially extending coupling slot and a pair of elastically-deformable securement members at lateral sides of the tang end portion that extend laterally outward as they extend axially from the tang end portion toward the tip end portion. The tang end portion of the cutting tool and the attachment mechanism are cooperatively configured such that upon full axial insertion of the tang end portion within the attachment mechanism between the first and second engagement surfaces, the pair of axially-spaced projections are positioned within the coupling slot, and the pair of laterally-spaced projections are positioned axially past at least a portion of the securement members.

In some embodiments, the cutting tool and the attachment mechanism are configured such that, upon full axial insertion of the tang end portion within the attachment mechanism, one of the projections of the pair of axially-spaced projections abuts an axial end of the coupling slot.

In some embodiments, the cutting tool and the attachment mechanism are configured such that, upon full axial insertion of the tang end portion within the attachment mechanism, the pair of laterally-spaced projections are positioned axially past a tip portion of the securement members that define the free ends thereof. In some such embodiments, the tip portions of the securement members define an end surface that extends laterally inwardly. In some such embodiments, the end surface of the tip portions of the securement members further extend axially as they extend laterally inwardly. In some embodiments, the cutting tool and the attachment mechanism are configured such that, upon full axial insertion of the tang end portion within the attachment mechanism, the pair of laterally-spaced projections are engaged with the end surface of the tip portion of the securement members.

In some embodiments, the cutting tool and the attachment mechanism are configured such that, upon full axial insertion of the tang end portion within the attachment mechanism, the securement member are in a deformed state. In some such embodiments, the securement members define a maximum lateral width in a natural state thereof that is greater than a minimum lateral width of the pair of laterally-spaced projections.

In some embodiments, the securement members and the pair of laterally-spaced projections are configured such that upon initial insertion of the tang portion into the attachment mechanism between the first and second engagement surfaces, the securement members are positioned between the laterally-spaced projections and are in a non-deformed natural state. In some such embodiments, the securement members and the pair of laterally-spaced projections are configured such that axial translation of the tang portion into the attachment mechanism between the first and second engagement surfaces from the initial insertion to the full axial insertion, the securement members are deformed laterally inwardly by the laterally-spaced projections into a deformed state. In some such embodiments, the securement members and the pair of laterally-spaced projections are configured such that axial translation of the tang portion into the attachment mechanism between the first and second engagement surfaces from the initial insertion to the full axial insertion, the securement members are deformed laterally inwardly by the laterally-spaced projections into a deformed state and then resiliently deform laterally outwardly when tip portions thereof are engaged with the pair of laterally-spaced projections.

In some embodiments, a minimum lateral width of the coupling slot is substantially the same as a maximum lateral width of the pair of axially-spaced projections. In some embodiments, the second engagement surface is planar. In some embodiments, the first engagement surface is planar. In some embodiments, the adjustment mechanism is configured to selectively apply a compressive force to the tang portion via the first and second engagement surfaces.

In some embodiments, the cutting tool is a cutting blade. In some embodiments, the cutting tool is a surgical cutting blade. In some embodiments, the cutting tool is a sagittal cutting blade. In some embodiments, the cutting edge is configured to cut material upon reciprocal lateral movement of the cutting tool.

In some embodiments, the cutting instrument comprises a powered end-effector configured to translate the cutting tool along a direction defined by the cutting edge. In some embodiments, the cutting instrument comprises a robotic arm configured to effectuate or facilitate movement of the cutting tool.

In another aspect, the present disclosure provides a cutting tool comprising a tang end portion, a tip end portion, and a cutting edge at a free end of the tip end portion configured to cut material upon movement of the cutting tool with the cutting edge in engagement with the material. The cutting tool defines an axial length extending between a free end of the tang end portion and the cutting edge. The tang end portion of the cutting tool comprises an axially-extending coupling slot and a pair of elastically-deformable securement members at lateral sides of the tang end portion that extend laterally outward as they extend axially from the tang end portion toward the tip end portion.

In some embodiments, tip portions of the securement members each define an end surface that extends laterally inwardly toward each other. In some such embodiments, the tip portions extend axially as they extend laterally inwardly.

In some embodiments, the cutting edge is configured to cut material upon reciprocal lateral movement of the cutting tool. In some embodiments, the cutting tool is a cutting blade. In some embodiments, the cutting tool is a planar cutting blade. In some embodiments, the cutting tool is a surgical cutting blade. In some embodiments, the cutting tool is a sagittal cutting blade.

In another aspect, the present disclosure provides a cutting tool attachment mechanism comprising, a first clamping member comprising a first cutting tool engagement surface, and a second clamping member comprising a second cutting tool engagement surface, a pair of axially-spaced projections extending past the second cutting tool engagement surface and a pair of laterally-spaced projections extending past the second cutting tool engagement surface. The cutting tool attachment mechanism further comprises an adjustment mechanism configured to selectively adjust the distance between the first and second cutting tool engagement surfaces via relative movement between the first and second clamping members. The attachment mechanism is configured to removably securely couple a tang portion of a cutting tool and the attachment mechanism together.

In some embodiments, the second cutting tool engagement surface is planar. In some such embodiments, the first cutting tool engagement surface is planar.

In some embodiments, the adjustment mechanism is configured to selectively apply a compressive force to the tang portion via the first and second cutting tool engagement surfaces.

In some embodiments, the attachment mechanism is coupled to a cutting instrument that is configured to effectuate or facilitate cutting movement of the attachment mechanism. In some such embodiments, the cutting instrument comprises a powered end-effector configured to translate the attachment mechanism along a cutting direction. In some such embodiments, the cutting instrument further comprises a robotic arm configured to effectuate or facilitate at least three-dimensional movement of the end-effector and the attachment mechanism.

It should be appreciated that all combinations of the foregoing aspects and additional concepts discussed in greater detail below (provided such concepts are not mutually inconsistent) are contemplated as being part of the inventive subject matter and to achieve the advantages disclosed herein.

These and other objects, features and advantages of this disclosure will become apparent from the following detailed description of the various aspects of the disclosure taken in conjunction with the accompanying drawings.

BRIEF DESCRIPTION OF THE DRAWINGS

These and other features, aspects, and advantages of the present disclosure will become better understood when the following detailed description is read with reference to the accompanying drawings, which are not necessarily drawn to scale and in which like reference numerals represent like aspects throughout the drawings, wherein.

DETAILED DESCRIPTION

Figure 1:
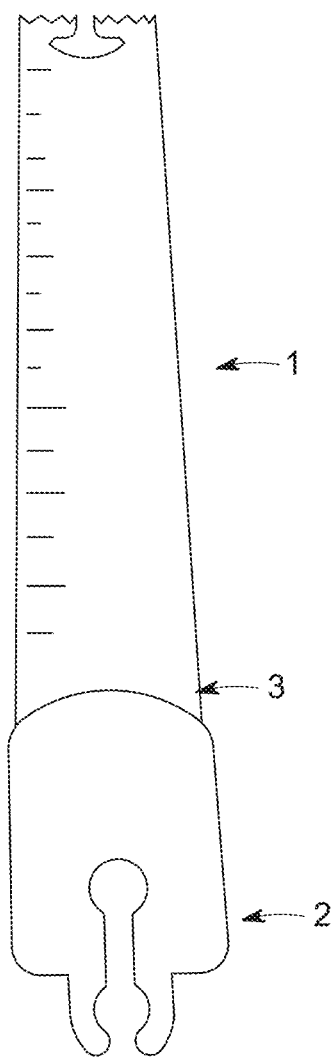
FIG. 1 illustrates, in one example, a top view of a prior art saw blade.

Aspects of the present disclosure and certain examples, features, advantages, and details thereof, are explained more fully below with reference to the non-limiting examples illustrated in the accompanying drawings. Descriptions of well-known materials, fabrication tools, processing techniques, etc., are omitted so as not to unnecessarily obscure the relevant details. It should be understood, however, that the detailed description and the specific examples, while indicating aspects of the disclosure, are given by way of illustration only, and are not by way of limitation. Various substitutions, modifications, additions, and/or arrangements, within the spirit and/or scope of the underlying inventive concepts will be apparent to those skilled in the art from this disclosure.

Approximating language, as used herein throughout disclosure, may be applied to modify any quantitative representation that could permissibly vary without resulting in a change in the basic function to which it is related. Accordingly, a value modified by a term or terms, such as "about" or "substantially," is not limited to the precise value specified. For example, these terms can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%. In some instances, the approximating language may correspond to the precision of an instrument for measuring the value. Any examples of operating or configuration parameters are not exclusive of other parameters of the disclosed embodiments.

Terminology used herein is for the purpose of describing particular examples only and is not intended to be limiting. As used herein, the singular forms "a", "an" and "the" are intended to include the plural forms as well, unless the context clearly indicates otherwise. Furthermore, references to "one example" are not intended to be interpreted as excluding the existence of additional examples that also incorporate the recited features. Moreover, unless explicitly stated to the contrary, the terms "comprising" (and any form of "comprise," such as "comprises" and "comprising"), "have" (and any form of "have," such as "has" and "having"), "include" (and any form of "include," such as "includes" and "including"), and "contain" (and any form of "contain," such as "contains" and "containing") are used as open-ended linking verbs. As a result, any examples that "comprises," "has," "includes" or "contains" one or more step or element possesses such one or more step or element, but is not limited to possessing only such one or more step or element.

As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances the modified term may sometimes not be appropriate, capable or suitable. For example, in some circumstances, an event or capacity can be expected, while in other circumstances the event or capacity cannot occur—this distinction is captured by the terms "may" and "may be."

The term "coupled" and like terms are used herein to refer to both direct and indirect connections. As used herein and unless otherwise indicated, the term "entirety" (and any other form of "entire") means at least a substantial portion, such as at least 95% or at least 99%. The term "entirety" (and any other form of "entire"), as used herein, is thereby not limited to 100%, unless otherwise indicated. As used herein, the term "layer"

Components, aspects, features, configurations, arrangements, uses and the like described, illustrated or otherwise disclosed herein with respect to any particular embodiment may similarly be applied to any other embodiment disclosed herein.

Figure 2:
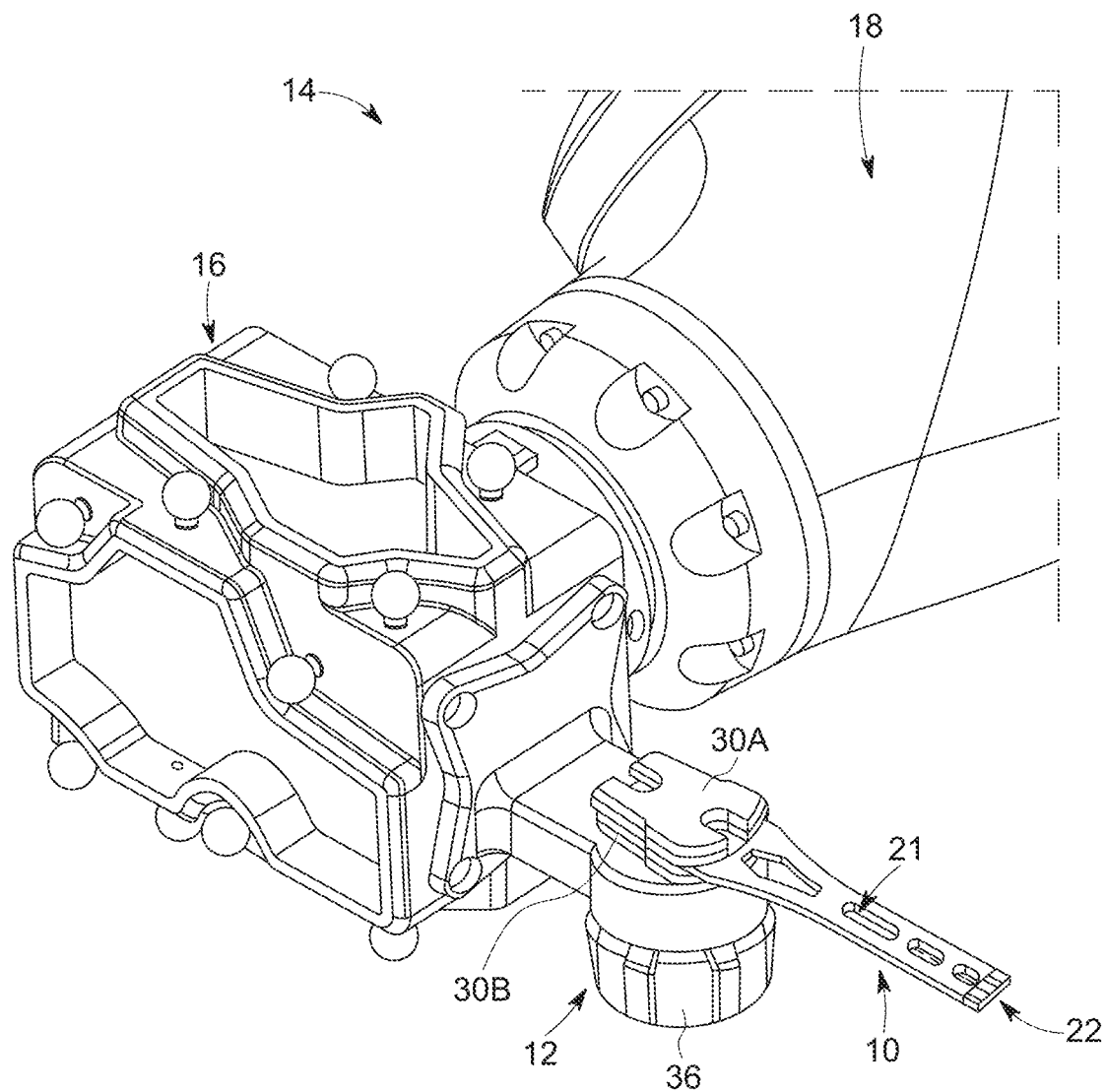
FIG. 2 illustrates, in one example, an elevational perspective view of a cutting instrument, a cutting tool attachment mechanism and a cutting tool, in accordance with one or more aspects of the present disclosure.

As shown in FIG. 2, the cutting tools 10, cutting instruments 14, cutting tool attachment mechanisms 12, and related tool attachment systems and methods are disclosed. The cutting instrument attachment mechanisms 12 and cutting tools 10 cooperate such that a user can quickly and reliably couple and decouple a cutting tool 10 with a cutting instrument 14 (which is part of, or couples to, one or more cutting instruments 14) via only one hand of a user. Furthermore, the cutting instrument attachment mechanism 12 and the cutting tool 10 prevent the cutting tool 10 from backing-out and becoming misalignment after the cutting tool 10 is initially inserted and coupled within the attachment mechanism 12 but prior to the cutting tool 10 being fully secured with the attachment mechanism 12 (via adjustment of the attachment mechanism 12). The cutting tool 10 and the attachment mechanism 12 are configured to provide for ease of placement, accuracy of placement, mitigated risk of poor placement, and ease of removal of the cutting tool 10 with the attachment mechanism 12 (and thereby a cutting instrument 14).

Figure 3:
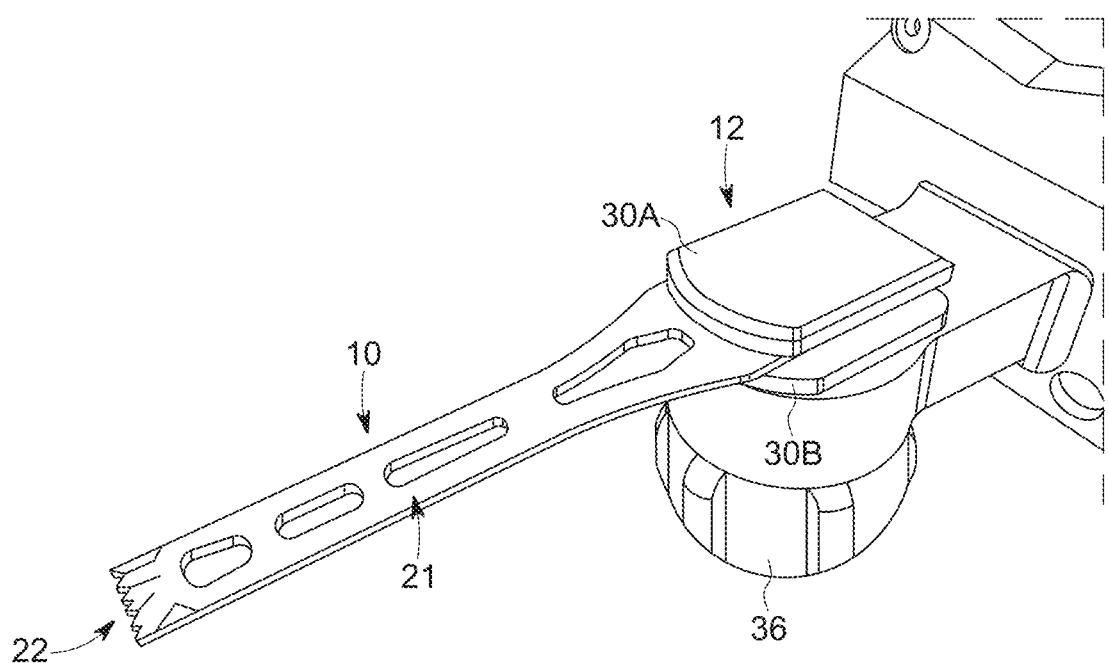
FIG. 3 illustrates an elevational perspective view of the cutting instrument and cutting tool attachment mechanism of FIG. 2, in accordance with one or more aspects of the present disclosure.
Figure 5:
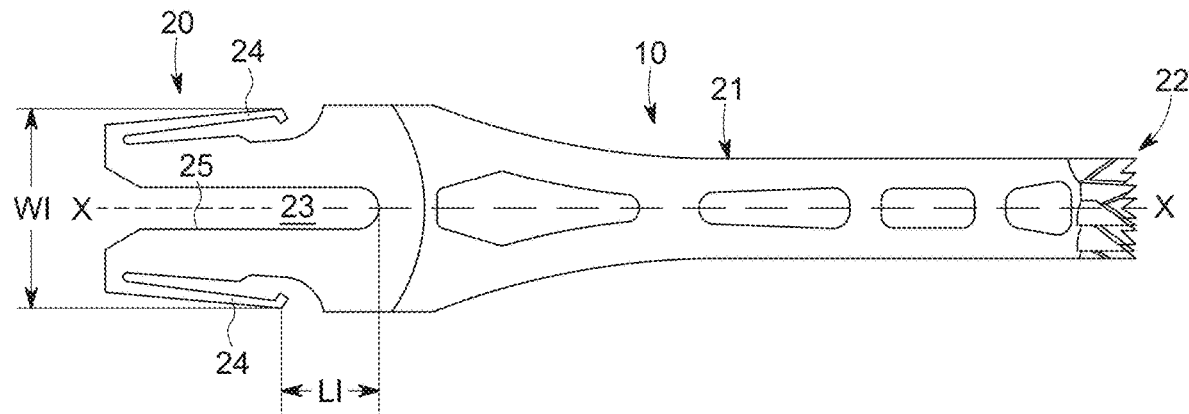
FIG. 5 illustrates, in one example, a top view of the cutting tool of FIG. 2, in accordance with one or more aspects of the present disclosure.

As shown in FIGS. 2, 3 and 5, the cutting tool 10 may be formed/configured as a saw blade, such as a sagittal saw blade configured to cut bone, cartilage and/or other tissues of a patient (e.g., a mammalian patient). For example, as shown in FIG. 5, the cutting tool 10 may be a planar saw blade that is longitudinally extended along an axis X-X with a tang portion 20 at one end, a tip portion 22 comprising a cutting edge, and a shaft or intermediate portion 21 extending between the tang portion 20 and the tip portion 22. The cutting edge at the tip portion 22 includes a plurality of cutting teeth (and/or abrasives) arranged laterally (extending across the axis X-X) along the plane of the blade (such as linearly or along an arc with a radius aligned with the axis X-X, for example), and that define the free end (i.e., the axial extent) of the cutting tool 10 at the tip portion 22.

The cutting tool 10 is configured such that when the blade moves in an oscillatory, back-and-forth pattern in the plane in which the blade is aligned, the cutting teeth of the tip portion 22 effectuate cutting. Consequently, when the cutting tool 10 is actuated by the cutting instrument 14, the blade teeth move in a back-and-forth pattern against the material to be cut (e.g., tissue or bone). As a consequence of this motion, and the forward pressure applied by the cutting instrument 14 (directly or indirectly), the teeth cut and separate the material to be cut.

It is expressly disclosed that the cutting tool 10 may not be configured as a sagittal saw blade, but rather a differing type of saw blade. For example, the cutting tool 10 may be configured as a reciprocating type saw blade with cutting teeth (and/or abrasives) arranged along an axially-extending lateral side of blade. As another example, the cutting tool 10 may be configured as any other blade-type cutting tool that utilizes the tang or attachment portion 20 to couple with an attachment mechanism 12 of a cutting instrument 14. Still further, the cutting tool 10 as a not-blade-type cutting tool (e.g., a rotary bit) that utilizes the tang or attachment portion 20 to couple with an attachment mechanism 12 of a cutting instrument 14.

The cutting instrument 14 may be configured as any instrument that that provides movement to the cutting tool 10 through the attachment mechanism 12. In some embodiments, the cutting instrument 14 may be a powered cutting instrument that comprises a motor (e.g., an electric motor) or other power mechanism that provides motion (e.g., selectively) to the cutting tool 10 along the cutting edge thereof. For example, as shown in FIG. 2, the cutting instrument 14 may be configured for use with a cutting tool 10 configures as a sagittal saw blade such that the cutting instrument 14 includes an end-effector or drive mechanism 16 configured to move the in an oscillatory, back-and-forth pattern in the plane in which the blade is aligned. However, the end-effector 16 may be configured to power or translate the cutting tool 10 in any other direction or pattern along which the cutting edge thereof is configured to cut.

In some embodiments, the end-effector 16 may include a motor and complementary control circuitry that regulates the actuation of the motor, and a drive system that transfers the power developed by the motor to the cutting tool 10 (via the attachment mechanism 12). More particularly, the drive system may be configured to convert rotary motion produced by the motor to the cutting tool 10 so that the cutting tool 10 moves along the direction of the cutting edge thereof.

In some embodiments, the cutting instrument 14 may be configured as a handheld instrument that is manually manipulated by a user. In some other embodiments, as shown in FIG. 2, the cutting instrument 14 may be configured as a robotic instrument. For example, the cutting instrument 14 may comprise an articulated robotic arm 18 that is coupled with, or includes, the drive mechanism 16 and the attachment mechanism 12. In some such embodiments, the robotic cutting instrument 14 may be configured with a hand-guided robotic arm 18 that moves the cutting tool 10 along its cutting pathway via the end-effector 16, but requires the user to manually guide the moving (e.g., reciprocating) cutting tool 10 to and/or through the material to be cut. In some other embodiments, the robotic cutting instrument 14 may be configured with an automated robotic arm 18 that moves the cutting tool 10 along its cutting pathway via the end-effector 16, but requires the user to manually guide the moving (e.g., reciprocating) cutting tool 10 to and/or through the material to be cut.

As shown in FIGS. 2-4 and 16-19, in some embodiments, the cutting tool attachment mechanism or connector 12 may comprise a clamping mechanism with first and second clamping or engagement members 30A, 30B and an adjustment member 36. The adjustment member 36 is configured to selectively adjust the relative position or space between engagement surfaces 31A, 31B of the engagement members 30A, 30B, respectively. In some embodiments, the adjustment member 36 may comprise a manual knob that adjusts a threaded connection between the clamping or engagement members 30A, 30B to adjust the relative position of the clamping or engagement members 30A, 30B, and thereby the space between engagement surfaces 31A, 31B. However, it is hereby contemplated that the clamping mechanism and the adjustment member 36 may form any arrangements or configurations that effectuate selective adjustment of the space between engagement surfaces 31A, 31B. For example, the clamping mechanism may comprise a cam mechanism, gear mechanism, linear actuator or any other configuration, mechanism or arrangement.

As explained further below, the clamping mechanism of the cutting tool attachment mechanism 12 may be configured to engage faces or sides of the cutting tool 10 (e.g., opposing faces), and potentially apply a compressive force thereto, as shown in FIGS. 2-4 and 19. The adjustment member 36 may thereby be utilized (e.g., manually) by a user to effectuate the clamping mechanism, and thereby "open" the clamping members 30A, 30B by enlarging the space between the engagement surfaces 31A, 31B, or "close" the clamping members 30A, 30B by minimizing the space between the engagement surfaces 31A, 31B. In some embodiments, the clamping mechanism may be configured to adjust the distance between the engagement surfaces 31A, 31B along a direction that extends normal to the plane of the cutting tool 10, for example.

Figure 4:
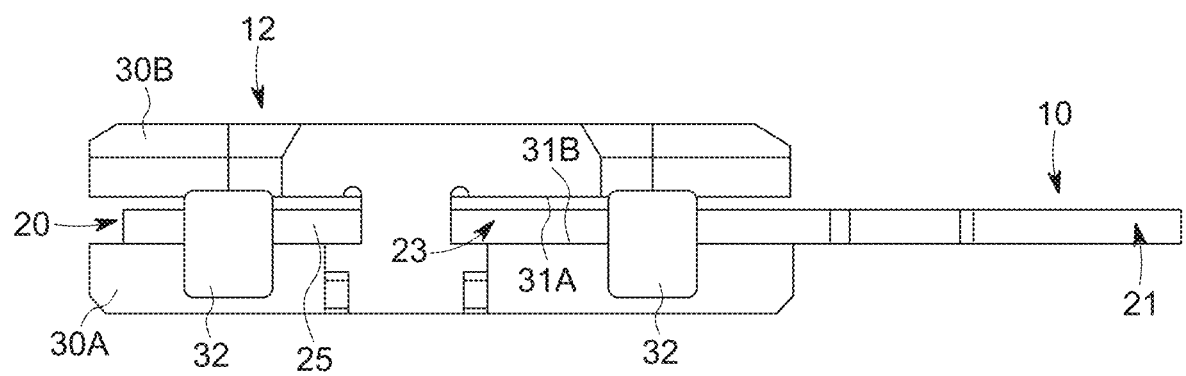
FIG. 4 illustrates, in one example, a cross-sectional view of the cutting tool and clamping members of the cutting tool attachment mechanism of FIG. 2, in accordance with one or more aspects of the present disclosure.
Figure 7:
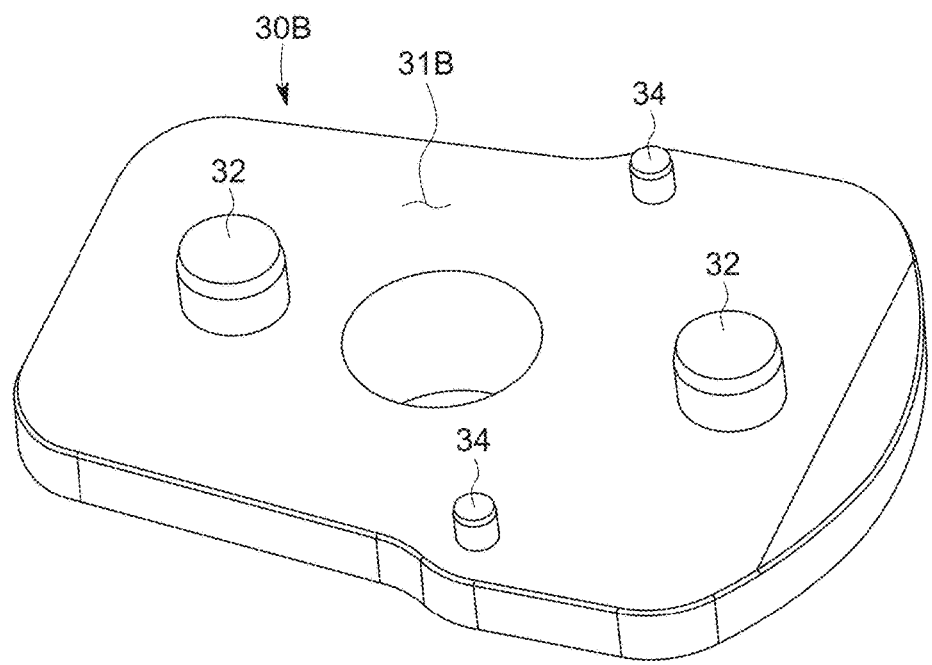
FIG. 7 illustrates, in one example, an elevational perspective view of a clamping member with alignment and securement projections of the cutting tool attachment mechanism of FIG. 2, in accordance with one or more aspects of the present disclosure.
Figure 8:
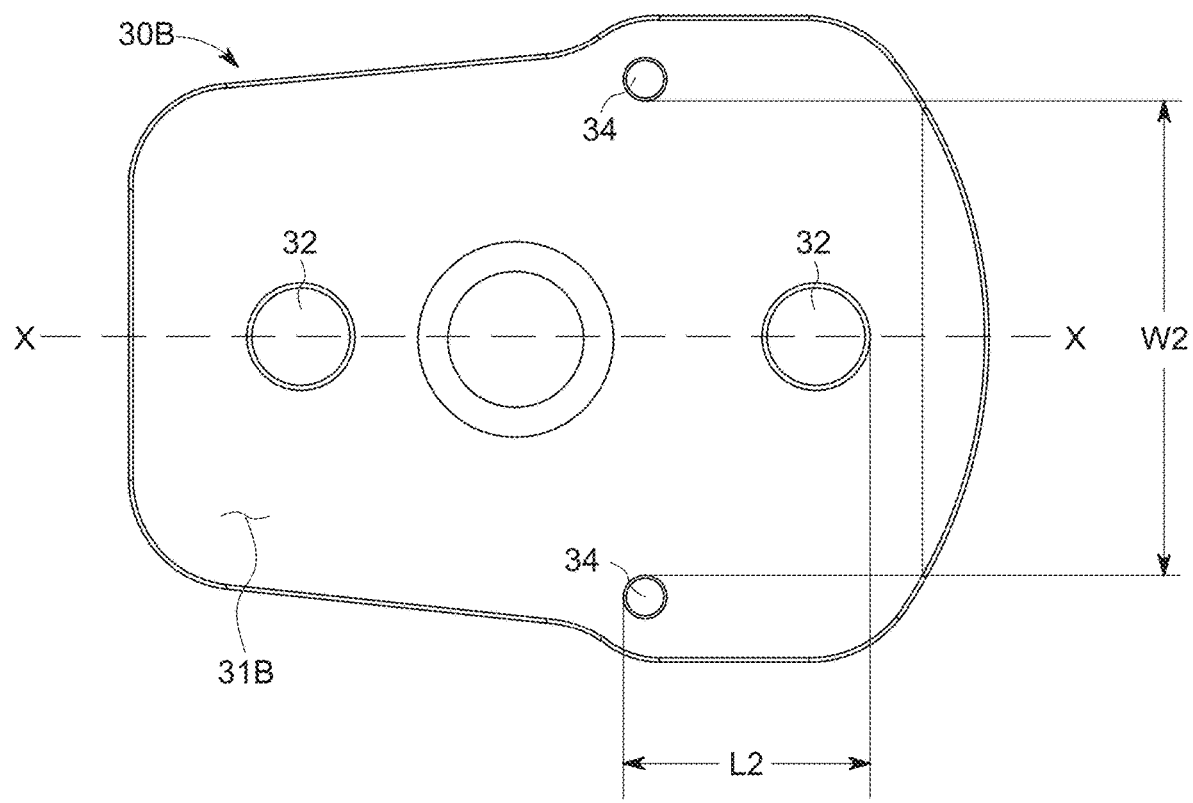
FIG. 8 illustrates, in one example, a top view of the clamping member and alignment and securement projections of FIG. 7, in accordance with one or more aspects of the present disclosure.

As shown in FIG. 4, the engagement surfaces 31A, 31B of the clamping members 30A, 30B may be configured to physically engage or abut faces of the cutting tool 10. In some embodiment, the first and second engagement surfaces 31A, 31B may be planar surfaces. As shown in FIGS. 7 and 8, the second engagement surface 31B of the second clamping member 30B may include axially-spaced alignment and securement projections 32 extending therefrom, and laterally-spaced back-out prevention projections 34 extending therefrom.

In the illustrative embodiment shown in FIGS. 7-15, the projections 32 and 34 are formed as cylindrical pin members that extend normally away from the second engagement surface 31B. However, the projections 32 and 34 may not be cylindrical, and may not extend normally from the engagement surface 31B. It is also noted that the projections 32 and 34 may be integral with the second clamping member 30B, or they may be separate and distinct components that are coupled to the second clamping member 30B. Further, the projections 32 and 34 may or may not include the same sizes, such as the same heights/thicknesses and diameters.

The axially-spaced alignment and securement projections 32 may include at least a first projection positioned proximate to a front end/side of the second engagement surface 31B, and a second projection positioned proximate to a back end/side of the second engagement surface 31B, as shown in FIGS. 7 and 8. The first and second axially-spaced alignment and securement projections 32, 32 may thereby be axially-spaced from each other. As shown in FIG. 8, the axial ends of the laterally-spaced back-out prevention projections 34 and the front projection 32 define a maximum second axial length L2.

As shown in FIGS. 7 and 8, the laterally-spaced back-out prevention projections 34 may include at least a first projection 34 positioned proximate to a first lateral end/side of the second engagement surface 31B, and a second projection positioned proximate to a second lateral end/side of the second engagement surface 31B. The first and second laterally-spaced back-out prevention projections 34, 34 may thereby be laterally-spaced from each other a second lateral width W2, as shown in FIG. 8. In some embodiments, the alignment and securement projections 32 may be positioned in a medial portion of the second engagement surface 31B, and positioned between the laterally-spaced back-out prevention projections 34.

The first engagement surface or side 31A of the first clamping member 30A may or may not include the axially-spaced alignment and securement projections 32 and/or the laterally-spaced back-out prevention projections 34. For example, in the illustrative exemplary embodiment shown in FIGS. 2-4 and 16-20, the engagement surface 31A is void of the projections 32 and the projections 34. In some such embodiments, the first engagement surface 31A may include cavities (e.g., depressions or apertures) that correspond in position and size with the projections 32 and the projections 34 such that the projections 32 and the projections 34 of the second engagement surface 31B can extend or nest therein (such as when a cutting tool is not positioned between the first and second engagement surfaces 31A, 31B and the first and second clamping members 30A, 30B are closed, or when the projections 32 and the projections 34 are thicker than the thickness of a cutting tool 10 being secured between the first and second engagement surfaces 31A, 31B). In some other embodiments, the first engagement surface 31A may be planar, and the projections 32 and the projections 34 of the second engagement surface 31B may engage, or be spaced from, the first engagement surface 31A when the first and second clamping members 30A, 30B are in a closed arrangement. In embodiments that include the projections 32 and/or the projections 34 extending from the first and second engagement surfaces 31A, 31B of the first and second clamping members 30A, 30B, the projections 32 and the projections 34 may be positioned to correspond to each other, and their heights/thicknesses may be configured such that the do not prevent the first and second engagement surfaces 31A, 31B from engaging a cutting tool 10 when it is positioned therebetween and the first and second clamping members 30A, 30B are in the closed arrangement.

Figure 6:
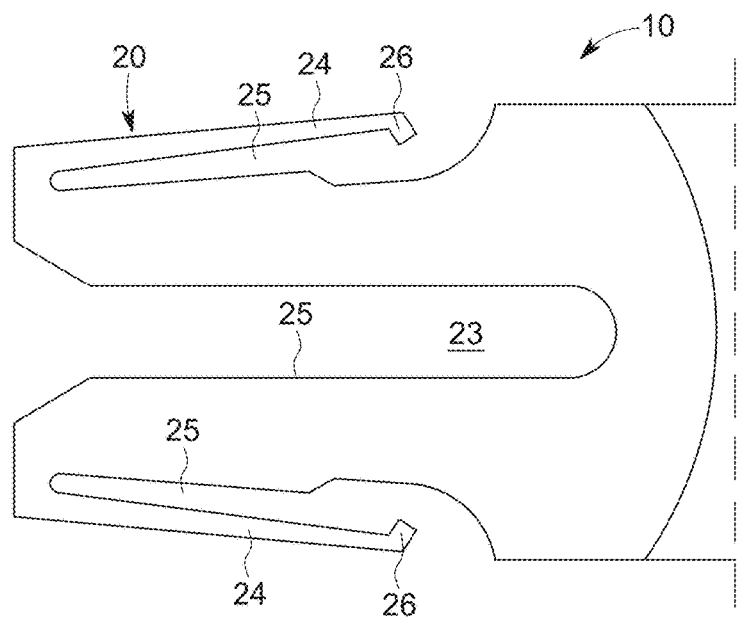
FIG. 6 illustrates, in one example, an enlarged top view of a tang portion of the cutting tool of FIG. 5, in accordance with one or more aspects of the present disclosure.

With reference to FIGS. 5 and 6, the tang portion 20 of the cutting tool 10 is configured such that aspects thereof cooperate with the axially-spaced alignment and securement projections 32 extending therefrom, and the laterally-spaced back-out prevention projections 34, as explained further below. Specifically, the tang portion 20 includes at least one elastically-deformable securement member or finger 24 on a lateral side of the tang portion 20, and a coupling slot 25 extending from the axial free end or side (e.g., extent) of the tang portion 20 of the cutting tool 10. As shown in FIGS. 5 and 6, in some embodiments the tang portion 20 includes a pair of the elastically-deformable securement members 24 at lateral sides of the tang portion 20.

The at least one elastically-deformable securement member 24 extends laterally outward as it extends axially toward the front end of the first engagement surface 31A (and thereby the front ends of the first and second clamping member 30A, 30B), as shown FIGS. 5 and 6. As also shown in FIGS. 5 and 6, a space 25 is formed laterally between a medial portion of the tang portion 20 (of the width thereof) and an inner side of each securement member 24. A securement member 24 is thereby able to be elastically deformed inwardly along the lateral direction or width of the tang portion 20, at least to a certain degree, as shown in FIG. 6.

The coupling slot 25 defines an inner medial cavity or opening 23 in the tang portion 20, which may be open at the axial end of the tang portion 20, as shown in FIGS. 5 and 6. As also shown in FIG. 5, the pair of lateral deformable securement members 24 define a maximum first lateral width W1 in their natural or neural state (i.e., non-deformed), and the coupling slot 25 may extend axially into the cutting tool 10 such that the axial ends of the deformable securement members 24 and the axial end of the coupling slot 25 define a maximum first axial length L1. The maximum first lateral width W1 of the pair of lateral deformable securement members 24 is greater than the second lateral width W2 of the first and second laterally-spaced back-out prevention projections 34, 34.

As explained further below with respect to FIGS. 9-19, the coupling slot 25 is configured to correspond to the axially-spaced alignment and securement projections 32 such that the projections 32 are positioned within the cavity 23 of the coupling slot 25 when the first and second clamping members 30A, 30B engage and couple the tang portion 20 of the cutting tool 10. In some embodiments, the maximum lateral width or diameter of the projections 32 may correspond to the minimum lateral width of the coupling slot 25. In this way, when the axially-spaced alignment and securement projections 32 are positioned within the coupling slot 25, the cutting tool 10 is prevented from moving laterally, and rotating along the plane of the blade (in all directions), with respect to the second engagement surface 31B of the second clamping member 30B (and, thereby, the first clamping member 30A). Further, the front projection 32 is configured such that when the front projection 32 engages the axial end of the coupling slot 25, the securement members 24 engage the projections 34 and prevent the cutting tool 10 from moving axially out from the front portion of the second clamping member 30B. In this way, front projection 32 and the coupling slot 25, and the securement members 24 and the projections 34, are cooperatively configured such that the cutting tool 10 is prevent from axial movement with respect to the second clamping member 30B (and, thereby, the first clamping member 30A) when the front projection 32 engages the axial end of the coupling slot 25.

An exemplary process of securely and reliably removably coupling the cutting tool 10 and the attachment mechanism 12 via the tang portion 20 and the first and second clamping members 30A, 30B is shown in FIGS. 9-21 and will now be described. It is noted that the first clamping member 30A is not shown in FIGS. 9-15 for explanatory purposes.

Figure 9:
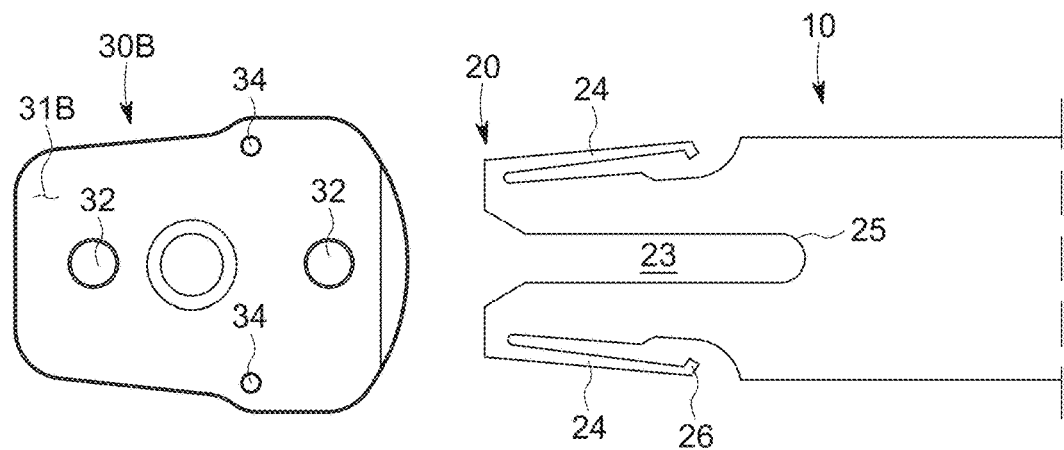
FIGS. 9-19 illustrate, in one example, the cutting tool and the cutting tool attachment mechanism of FIG. 2 sequentially becoming removably securely coupled together, in accordance with one or more aspects of the present disclosure.

As shown in FIG. 9, to utilize the attachment mechanism 12 to securely and reliably removably coupling the cutting tool 10 attach the cutting tool to the cutting instrument 14, the tang portion 20 of the cutting tool 10 may initially be substantially aligned with the space between the first and second engagement surfaces 31A, 31B of the first and second clamping members 30A, 30B, and inserted therebetween with the coupling slot 25 being substantially aligned with the front projection 32. It is noted that the space between the first and second engagement surfaces 31A, 31B may be adjusted, such as via the adjustment member 36, to be slightly larger than the thickness of the cutting tool 10 so that the tang portion 20 can be inserted therebetween, and potentially ensure the tang portion 20 cannot travel along the thickness direction over the projections 32 (and the projections 34) (e.g., between the projections 32 and the first engagement surface 31A).

Figure 10:
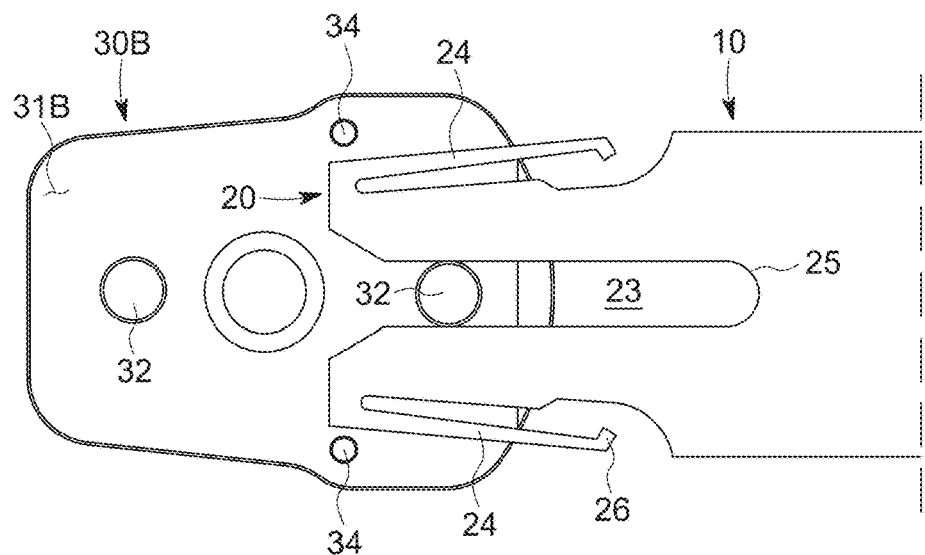
Figure 11:
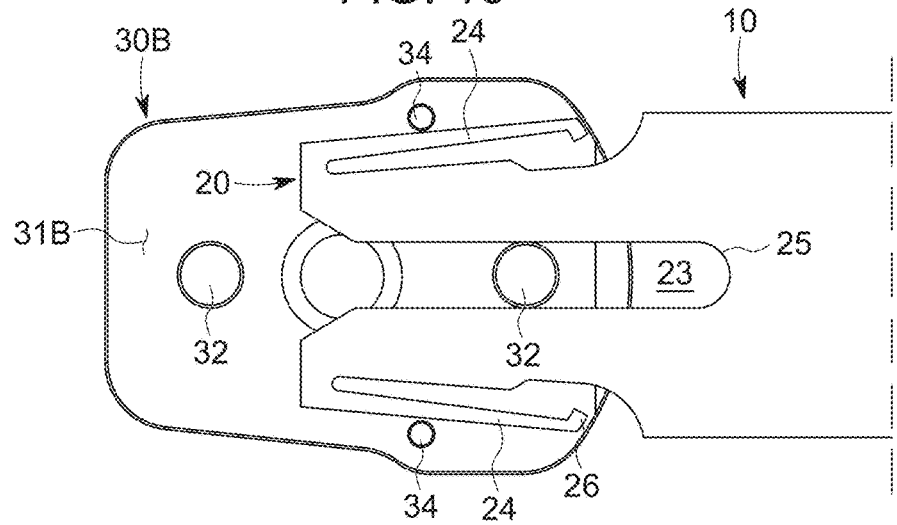
Figure 16:
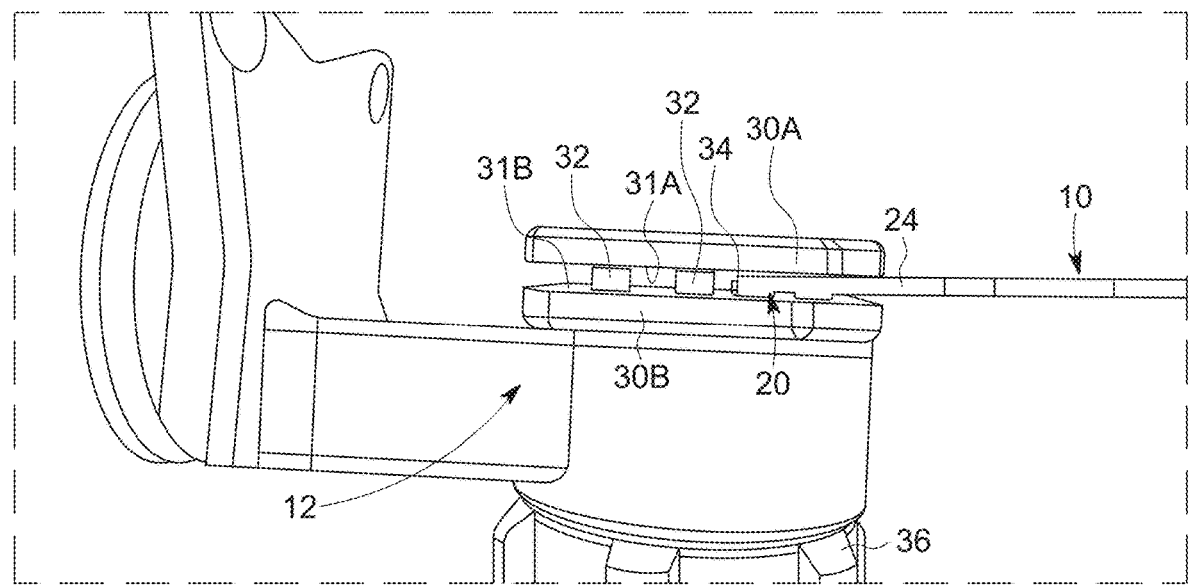
Figure 17:
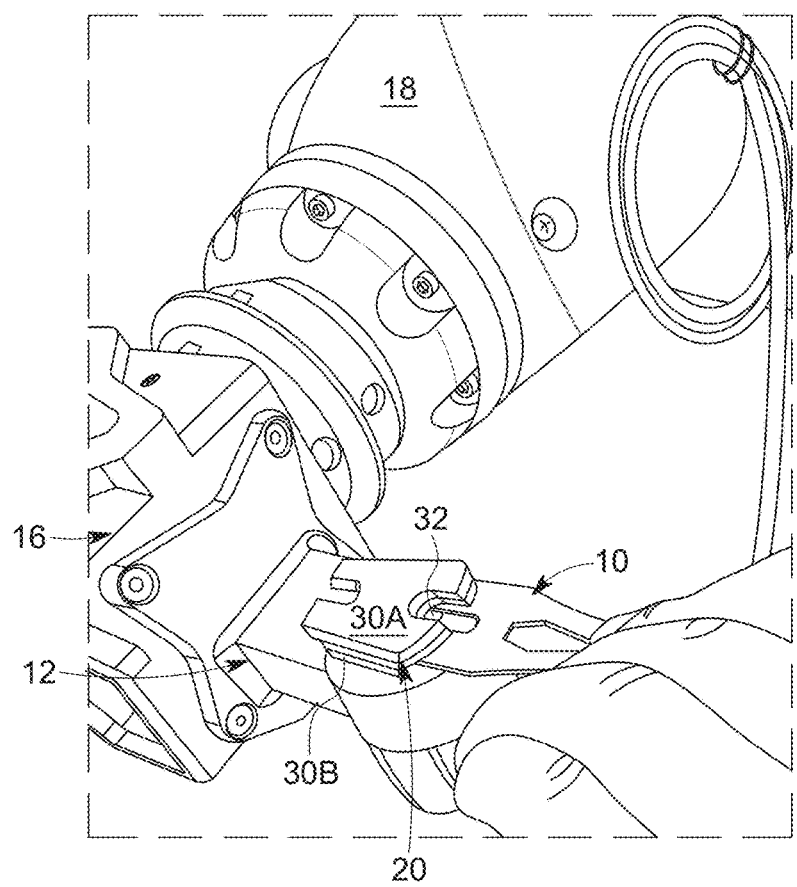

As shown in FIGS. 10, 16 and 17, the tang portion 20 can be translated along the second engagement surface 31B, or otherwise axially inserted into the attachment mechanism 12 between the first and second engagement surfaces 31A, 31B, such that the coupling slot 25 is translated over the front projection 32 such that the front projection 32 is positioned within the cavity 23. It is noted that the axial end of the coupling slot 25 may be relatively wide, and potentially angled medially as it extends axially, so facilitate and/or guide the coupling slot 25 over/around the front projection 32, as shown in FIG. 10. The axial end of the tang portion 20 may be sized in the lateral or width direction such that, upon initial insertion and for a limited period of axial travel of the cutting tool 10, the laterally-spaced back-out prevention projections 34 are not engaged by the tang portion 20. However, as shown in FIG. 11, with the front projection being positioned with the coupling slot 25, the cutting tool 10 is further inserted axially into the attachment mechanism 12 between the first and second engagement surfaces 31A, 31B to such an extent that the lateral outward sides of the securement members 24 engage the laterally-spaced back-out prevention projections 34.

Figure 12:
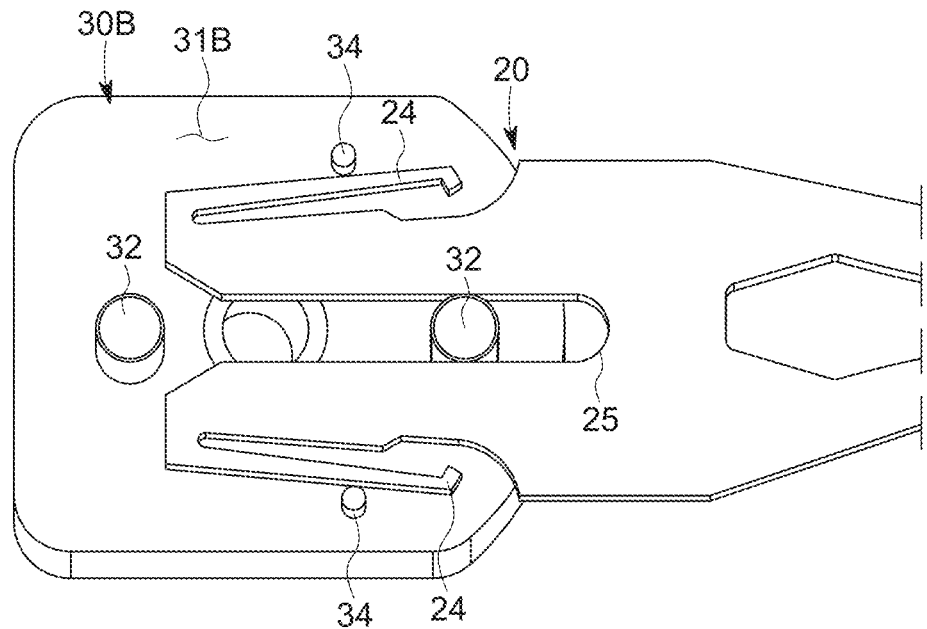
Figure 13:
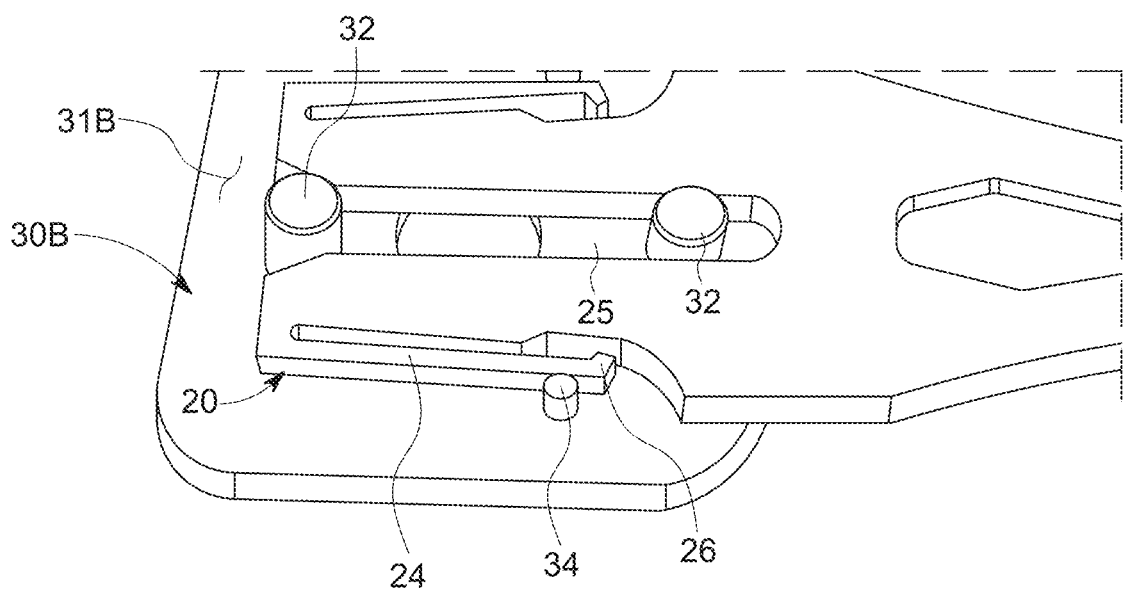
Figure 14:
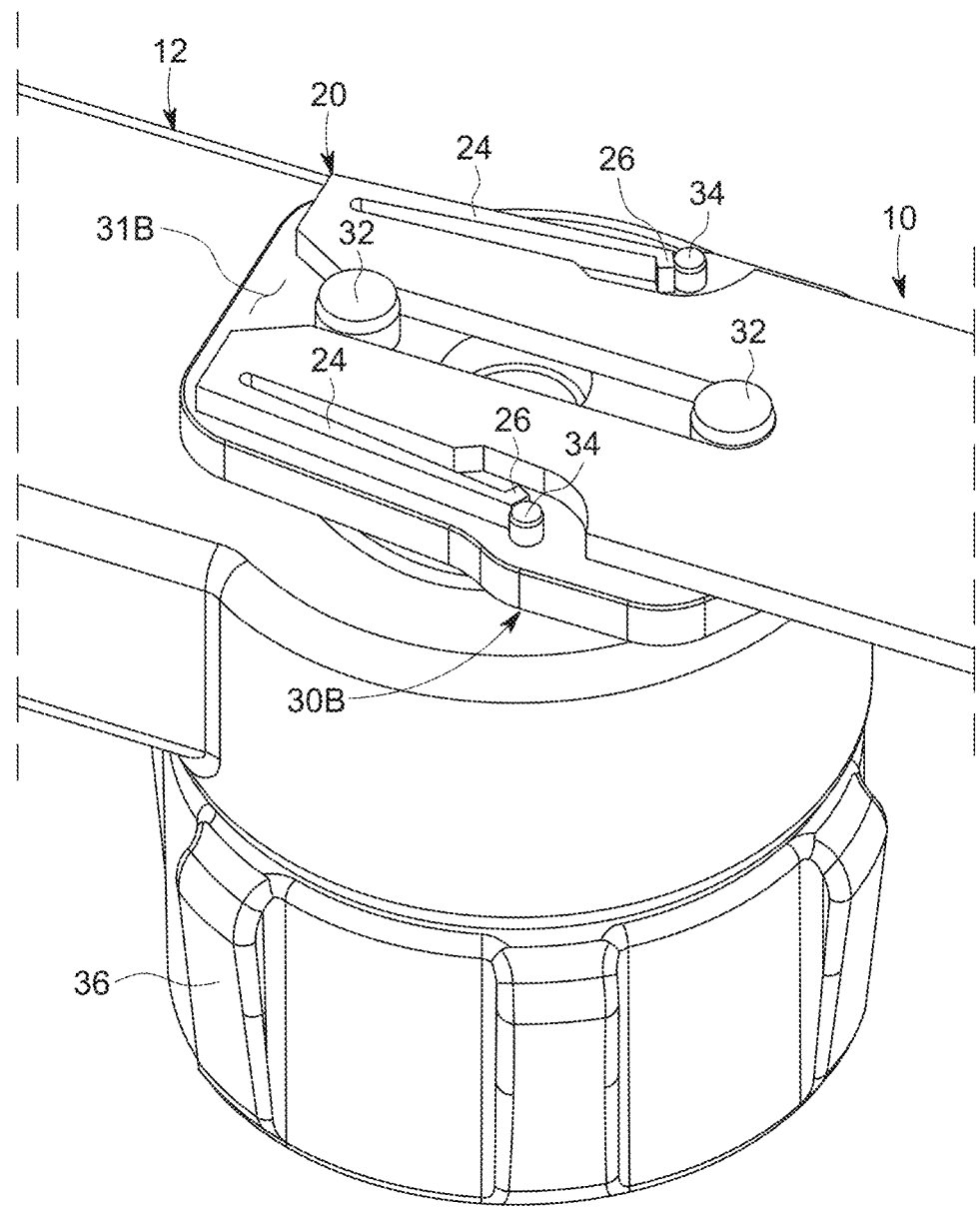
Figure 15:
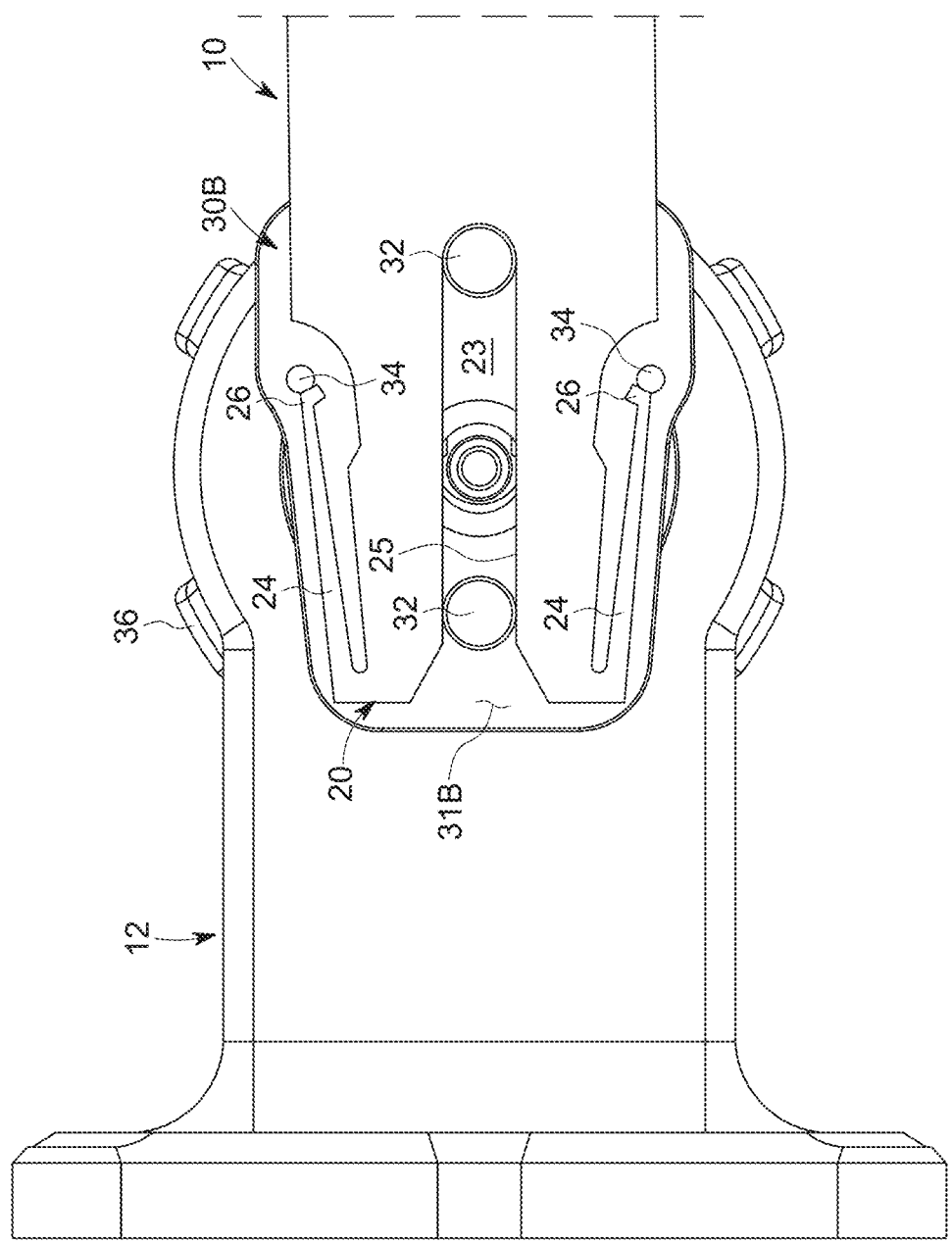

As shown in FIGS. 12 and 13, once the cutting tool 10 is positioned within the attachment mechanism 12 such that the securement members 24 engage the projections 34, further axial translation of the cutting tool 10 into the attachment mechanism 12 causes the projections 34 to elastically deform the securement members 24 inward toward the medial portion of the tang portion 20 (i.e., medially along the width or lateral direction) (and the front projection 32 becomes positioned axially deeper into the coupling slot 25). As shown in FIGS. 14 and 15, the cutting tool 10 can be further axial translated into the attachment mechanism 12 such that the tip portions 26 of the securement members 24 reach the laterally-spaced back-out prevention projections 34, the rear projection 32 becomes positioned within the coupling slot 25, and the front projection 32 engages the axial end of the coupling slot 25.

The tip portions 26 of the securement members 24 may be angled inwardly laterally (i.e., medially) as they extend axially, as shown in FIGS. 6, 14 and 15. Specifically, an axial end face, surface or side of the tip portions 26 of the securement members 24 may be angled inwardly laterally (i.e., medially) as they extend axially. As such, when the tip portions 26 of the securement members 24 reach the projections 34 and are further axially translated, the tip portions 26 allow the securement members 24 to elastically/resiliently deform laterally outwardly toward their neutral state/position into a locking state or position. Such elastic/resilient movement of the securement members 24, and/or the engagement of the tip portions 26 and the projections 34, causes an audible and/or tactile indication or feedback, which signifies to the user that the cutting tool 10 has been properly and fully inserted into the attachment mechanism 12.

Further, the first axial length L1 between the tip portions 26 of the deformable securement members 24 and the axial end of the coupling slot 25 and the second axial length L2 between the axial ends of the laterally-spaced back-out prevention projections 34 and the front projection 32 are relatively sized such that when the front projection 32 engages the axial end of the coupling slot 25, the projections 34 are engaged with the tip portions 26 (or are positioned axially past at least a portion of the securement members 24). As the tip portions 26 extend laterally inwardly (i.e., toward the medial portion of the tang portion 20), the projections 34 are positioned axially past at least a portion of the securement members 24 when the front projection 32 engages the axial end of the coupling slot 25, and thereby prevent the cutting tool 10 from translating axially forward and back out of the attachment mechanism 12 (i.e., axially fixed).

The securement members 24 are elastically deformed or depressed into the deformed state during initial insertion of the cutting tool 10 into the cutting tool attachment mechanism 12, and resiliently deform from the deformed state into the locking state upon the cutting tool 10 being fully inserted into the cutting tool attachment mechanism 12. In the locking state of the securement members 24, the cutting tool 10 is reliably and securely releasably coupled with the cutting tool attachment mechanism 12 (and thereby the cutting instrument 14) as the securement members 24 provide a locking force that prevents backout of the cutting tool 10 from the attachment mechanism 12. Further, as shown in FIG. 17, the securement members 24, in their locking state, prevent backout of the cutting tool 10 prior to adjustment of the attachment mechanism 12 (e.g., via the adjustment member 36) such that the first and second engagement surfaces 31A, 31B engage (and potentially apply a compressive force to) the tang portion 20.

Figure 18:
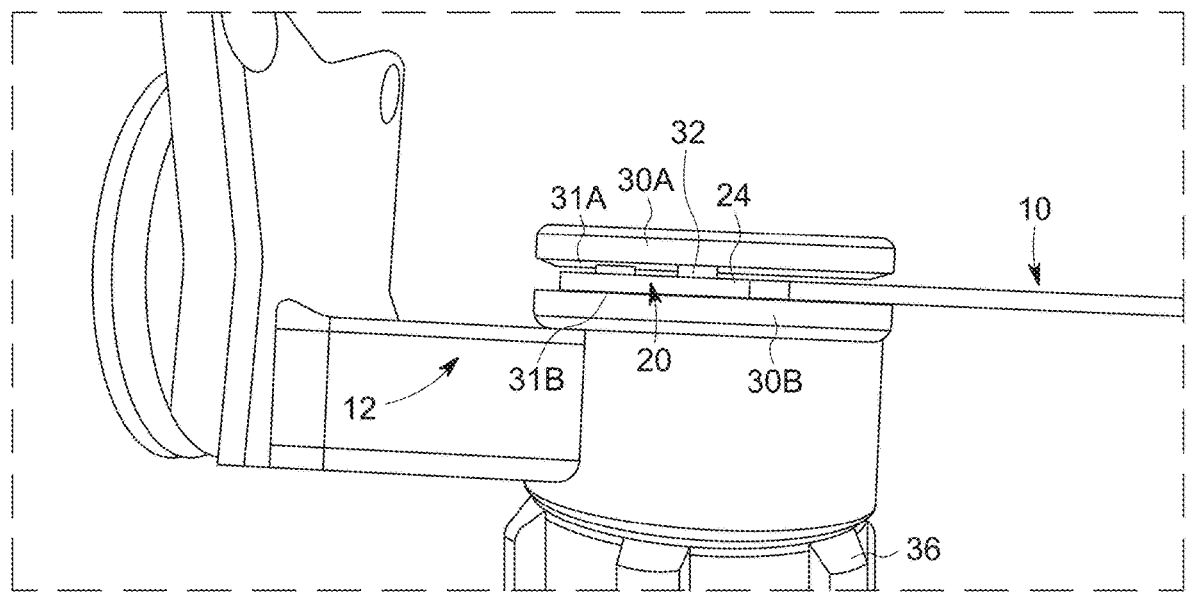
Figure 19:
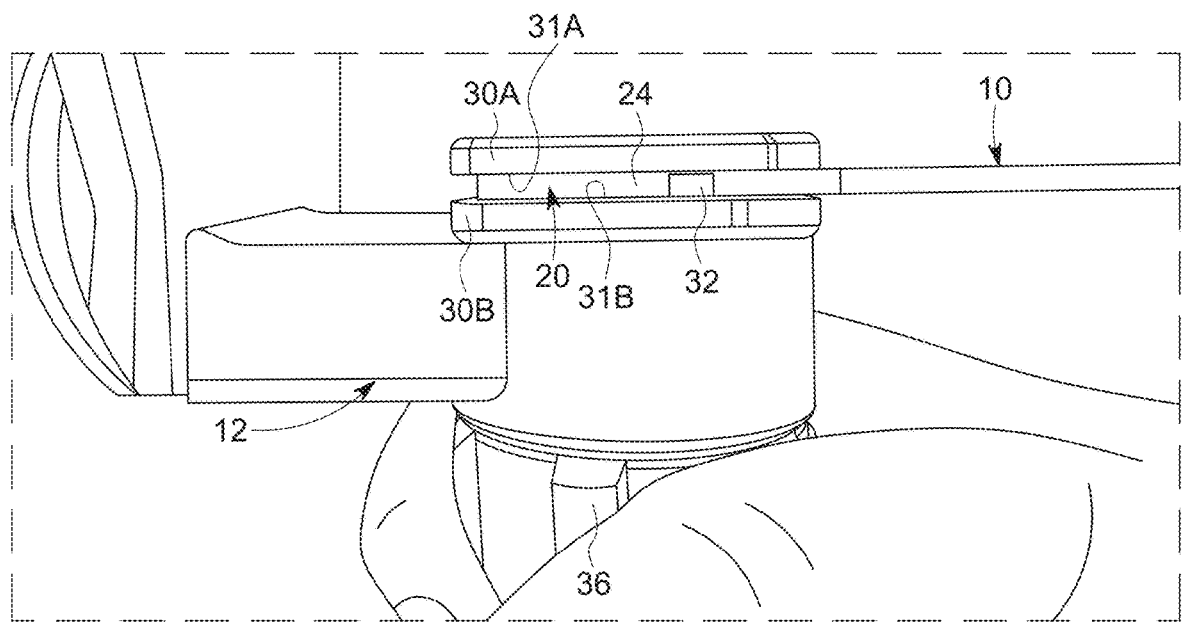

As shown in FIGS. 18 and 19, after the cutting tool 10 is fully inserted into the attachment mechanism 12 such that the cutting tool 10 is reliably releasably coupled with the cutting tool attachment mechanism 12 (and thereby the cutting instrument 14) via the securement members 24 and the laterally-spaced back-out prevention projections 34, and the coupling slot 25 and the axially-spaced alignment and securement projections 32, the attachment mechanism 12 can be adjusted (e.g., via the adjustment member 36) such that the first and second engagement surfaces 31A, 31B engage (and potentially apply a compressive force to) the tang portion 20 such that the attachment mechanism 12 reliably releasably locks the cutting tool 10 and the attachment mechanism 12 together.

Figure 20:
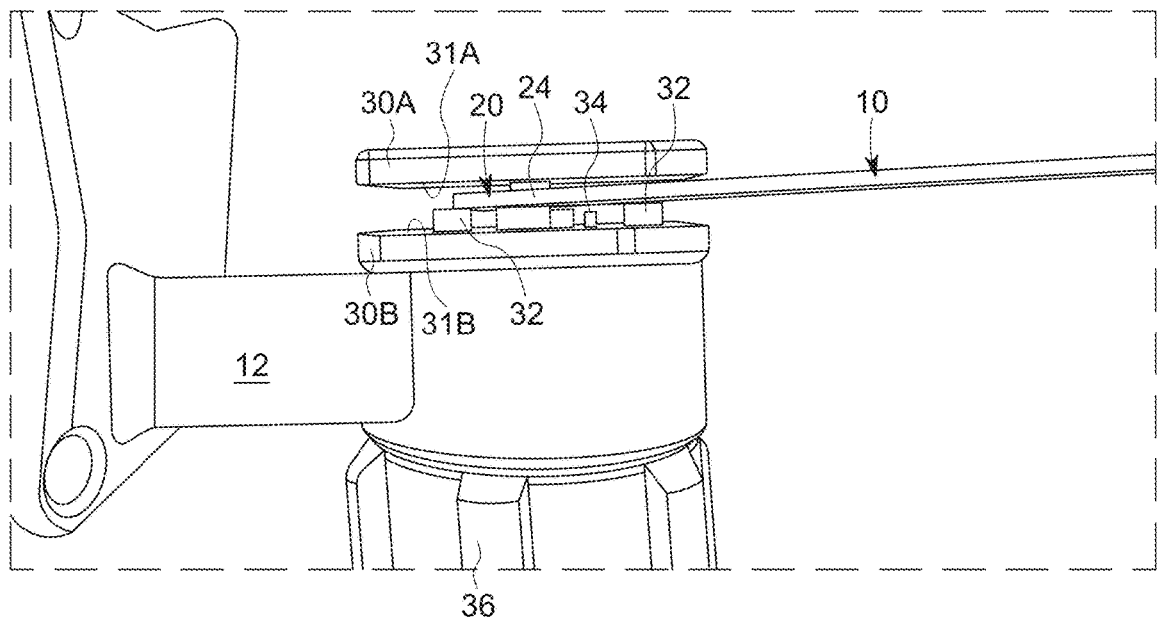
FIGS. 20 and 21 illustrate, in one example, decoupling cutting tool and the cutting tool attachment mechanism of FIG. 2, in accordance with one or more aspects of the present disclosure.
Figure 21:
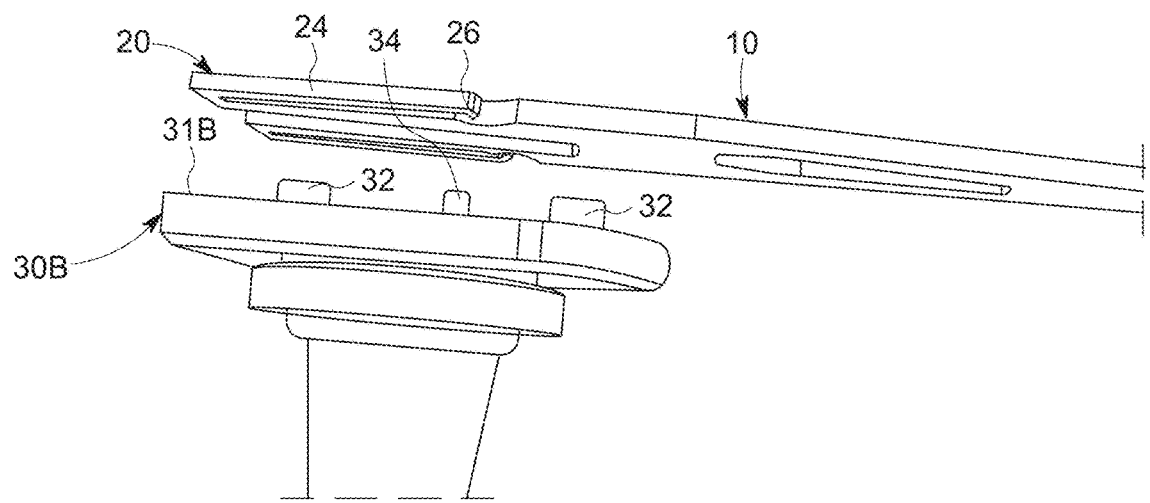

After use of the cutting tool 10 to cut a material (e.g., bone or other tissue), the attachment mechanism 12 can be adjusted (e.g., via the adjustment member 36) such that the first and second engagement surfaces 31A, 31B disengage from the tang portion 20 such that a space is formed between at least one previously-engaged face of the cutting tool 10 and at the first and/or second engagement surface 31A, 31B, as shown in FIG. 20. The cutting tool 10 can then be removed from the attachment mechanism 12 (between the first and second clamping members 30A, 30B by translating the cutting tool 10 along the thickness thereof such that tang portion 20 is translated along and past the projection 32 and the projections 34, as shown in FIGS. 20 and 21.

It is to be understood that the above description is intended to be illustrative, and not restrictive. For example, the above-described examples (and/or aspects thereof) may be used in combination with each other. In addition, many modifications may be made to adapt a particular situation or material to the teachings of the various examples without departing from their scope. While dimensions and types of materials may be described herein, they are intended to define parameters of some of the various examples, and they are by no means limiting to all examples and are merely exemplary. Many other examples will be apparent to those of skill in the art upon reviewing the above description. The scope of the various examples should, therefore, be determined with reference to the appended claims, along with the full scope of equivalents to which such claims are entitled.

In the appended claims, the terms "including" and "in which" are used as the plain-English equivalents of the respective terms "comprising" and "wherein." Moreover, in the following claims, the terms "first," "second," and "third," etc. are used merely as referee labels, and are not intended to impose numerical, structural or other requirements on their objects. Forms of term "based on" herein encompass relationships where an element is partially based on as well as relationships where an element is entirely based on. Forms of the term "defined" encompass relationships where an element is partially defined as well as relationships where an element is entirely defined. Further, the limitations of the following claims are not written in means-plus-function format and are not intended to be interpreted based on 35 U.S.C. § 112, sixth paragraph, unless and until such claim limitations expressly use the phrase "means for" followed by a statement of function cavity of further structure. It is to be understood that not necessarily all such objects or advantages described above may be achieved in accordance with any particular example. Thus, for example, those skilled in the art will recognize that the devices, systems and methods described herein may be embodied or carried out in a manner that achieves or optimizes one advantage or group of advantages as taught herein without necessarily achieving other objects or advantages as may be taught or suggested herein.

While the disclosure has been described in detail in connection with only a limited number of examples, it should be readily understood that the disclosure is not limited to such disclosed examples. Rather, this disclosure can be modified to incorporate any number of variations, alterations, substitutions or equivalent arrangements not heretofore described, but which are commensurate with the spirit and scope of the disclosure. Additionally, while various examples have been described, it is to be understood that aspects of the disclosure may include only one example or some of the described examples. Also, while some disclosure are described as having a certain number of elements, it will be understood that the examples can be practiced with less than or greater than the certain number of elements.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

We claim:

1. A system comprising:
   a cutting tool comprising a tang end portion, a tip end portion, and a cutting edge on the tip end portion configured to cut material upon movement of the cutting tool with the cutting edge in engagement with the material, the cutting tool having an axial length extending between the tang end portion and the cutting edge; and
   a cutting instrument comprising an attachment mechanism configured to removably securely couple the cutting tool and the cutting instrument together, the cutting instrument configured to effectuate or facilitate the movement of the cutting tool,
   wherein the attachment mechanism comprises:
      a first clamping member comprising a first engagement surface;
      a second clamping member comprising a second engagement surface, a pair of axially-spaced projections extending past the second engagement surface and a pair of laterally-spaced projections extending past the second engagement surface; and
      an adjustment mechanism configured to selectively adjust the distance between the first and second engagement surfaces via relative movement between the first and second clamping member,
   wherein the tang end portion of the cutting tool comprises an axially extending coupling slot and a pair of elastically-deformable securement members at lateral sides of the tang end portion that extend laterally outward as they extend axially from the tang end portion toward the tip end portion, and
   wherein the tang end portion of the cutting tool and the attachment mechanism are cooperatively configured such that upon full axial insertion of the tang end portion within the attachment mechanism between the first and second engagement surfaces, the pair of axially-spaced projections are positioned within the coupling slot, and the pair of laterally-spaced projections are positioned axially past at least a portion of the securement members, and
   wherein the securement members and the pair of laterally-spaced projections are configured such that upon initial insertion of the tang portion into the attachment mechanism between the first and second engagement surfaces the securement members are positioned between the laterally-spaced projections and are in a non-deformed natural state, and such that axial translation of the tang portion into the attachment mechanism between the first and second engagement surfaces from the initial insertion to the full axial insertion the securement members are deformed laterally inwardly by the laterally-spaced projections into a deformed state.

2. The system of claim 1, wherein the cutting tool and the attachment mechanism are configured such that, upon full axial insertion of the tang end portion within the attachment mechanism, one of the projections of the pair of axially-spaced projections abuts an axial end of the coupling slot.

3. The system of claim 1, wherein the cutting tool and the attachment mechanism are configured such that, upon full axial insertion of the tang end portion within the attachment mechanism, the pair of laterally-spaced projections are positioned axially past a tip portion of the securement members that define free ends thereof.

4. The system of claim 3, wherein the tip portion of the securement members define an end surface that extends laterally inwardly.

5. The system of claim 4, wherein the end surface of the tip portions of the securement members further extend axially as they extend laterally inwardly.

6. The system of claim 3, wherein, upon full axial insertion of the tang end portion within the attachment mechanism, the pair of laterally-spaced projections are engaged with an end surface of the tip portion of the securement members.

7. The system of claim 6, wherein the cutting tool and the attachment mechanism are configured such that, upon full axial insertion of the tang end portion within the attachment mechanism, the securement members are in a deformed state.

8. The system of claim 1, wherein the securement members define a maximum lateral width in a natural state thereof that is greater than a minimum lateral width of the pair of laterally-spaced projections.

9. The system of claim 1, wherein the securement members and the pair of laterally-spaced projections are configured such that axial translation of the tang portion into the attachment mechanism between the first and second engagement surfaces from the initial insertion to the full axial insertion, the securement members are deformed laterally inwardly by the laterally-spaced projections into a deformed state and then resiliently deform laterally outwardly when tip portions thereof are engaged with the pair of laterally-spaced projections.

10. The system of claim 1, wherein a minimum lateral width of the coupling slot is substantially the same as a maximum lateral width of the pair of axially-spaced projections.

11. The system of claim 1, wherein the second engagement surface is planar.

12. The system of claim 1, wherein the first engagement surface is planar.

13. The system of claim 1, wherein the adjustment mechanism is configured to selectively apply a compressive force to the tang end portion via the first and second engagement surfaces.

14. The system of claim 1, wherein the cutting tool is a cutting blade.

15. The system of claim 14, wherein the cutting tool is a surgical cutting blade.

16. The system of claim 15, wherein the cutting tool is a sagittal surgical cutting blade.

17. The system of claim 14, wherein the cutting edge is configured to cut material upon reciprocal lateral movement of the cutting tool.

18. The system of claim 1, wherein the cutting instrument comprises a powered end-effector configured to translate the cutting tool along a direction defined by the cutting edge.

19. The system of claim 1, wherein the cutting instrument comprises a robotic arm configured to effectuate or facilitate movement of the cutting tool, and a powered end-effector coupled to an end segment of the robotic arm configured to translate the cutting tool along a cutting pathway defined by the cutting edge.

20. The system of claim 1, wherein the cutting instrument is a surgical robot system.

* * * * *